United States Patent
Trübel et al.

(10) Patent No.: US 11,763,924 B2
(45) Date of Patent: Sep. 19, 2023

(54) SUPPORTING PATIENTS IN THE REPEATED TAKING OF DRUGS

(71) Applicant: Bayer Aktiengesellschaft, Leverkusen (DE)

(72) Inventors: Hubert Trübel, Wuppertal (DE); Philip Patrick Böhme, Marburg (DE); Martin Van Eickels, Berlin (DE); Wilfried Dinh, Rhede (DE); Frank Kramer, Wülfrath (DE); Carlos Castellon, Berlin (DE)

(73) Assignee: Bayer Aktiengesellschaft, Leverkusen (DE)

( * ) Notice: Subject to any disclaimer, the term of this patent is extended or adjusted under 35 U.S.C. 154(b) by 772 days.

(21) Appl. No.: 16/495,816

(22) PCT Filed: Mar. 16, 2018

(86) PCT No.: PCT/EP2018/056651
§ 371 (c)(1),
(2) Date: Sep. 19, 2019

(87) PCT Pub. No.: WO2018/172204
PCT Pub. Date: Sep. 27, 2018

(65) Prior Publication Data
US 2020/0027540 A1 Jan. 23, 2020

(30) Foreign Application Priority Data
Mar. 23, 2017 (EP) .................................... 17162556
Oct. 10, 2017 (EP) .................................... 17195605

(51) Int. Cl.
*G16H 20/10* (2018.01)
*G16H 80/00* (2018.01)
*A61B 5/00* (2006.01)

(52) U.S. Cl.
CPC .......... *G16H 20/10* (2018.01); *A61B 5/0002* (2013.01); *A61B 5/4833* (2013.01); *A61B 5/7465* (2013.01); *G16H 80/00* (2018.01)

(58) Field of Classification Search
CPC ...... G16H 20/10; G16H 80/00; A61B 5/0002; A61B 5/4833; A61B 5/7465; A61B 5/746
See application file for complete search history.

(56) References Cited

U.S. PATENT DOCUMENTS

| 2006/0242295 A1* | 10/2006 | Husemann | H04W 88/14 |
| | | | 709/224 |
| 2009/0299924 A1* | 12/2009 | Bauer | G16H 40/67 |
| | | | 706/46 |
| 2015/0178469 A1 | 6/2015 | Park | |

FOREIGN PATENT DOCUMENTS

| JP | 2014204744 A | 10/2014 |
| JP | 2015228082 A | 12/2015 |

(Continued)

OTHER PUBLICATIONS (Cramm, Heidi; Seguin, Josee; Adler, Roselle. iDevices and occupational therapy/L'utilite des iDevices en ergotherapie. Occupational Therapy Now 13.3: 19(8). Canadian Association of Occupational Therapists. (May 2011-Jun. 2011) (Year: 2011).*

(Continued)

*Primary Examiner* — Linh Giang Le
(74) *Attorney, Agent, or Firm* — MORRISON & FOERSTER LLP (57) ABSTRACT

The invention relates to the technical field of supporting patients in the repeated taking of drugs within the context of a therapeutic treatment. The invention relates to a method, to a system, and to a computer program product that monitor the taking of drugs by a patient and inform the patient or a (Continued)

doctor or another person if a drug portion should not be taken in order to thus optimize the effectiveness of the treatment or reduce risks.

13 Claims, 7 Drawing Sheets

(56) References Cited

FOREIGN PATENT DOCUMENTS

| WO | WO2007081947 A2 | 7/2007 | |
|---|---|---|---|
| WO | WO2010104841 A2 | 9/2010 | |
| WO | WO-2011097313 A1 * | 8/2011 | ......... G06F 19/3481 |
| WO | WO2011097313 A1 | 8/2011 | |

OTHER PUBLICATIONS

International Search Report dated Jun. 4, 2018 for International Application No. PCT/EP2018/056651, filed Mar. 16, 2018, 4 pages.

* cited by examiner

SUPPORTING PATIENTS IN THE REPEATED TAKING OF DRUGS

CROSS REFERENCE TO RELATED APPLICATIONS

This application is a national stage application under 35 U.S.C. § 371 of International Application No. PCT/EP2018/056651, filed internationally on Mar. 16, 2018, which claims benefit of European Application No. 17162556.9, filed Mar. 23, 2017 and European Application No. 17195605.5, filed Oct. 10, 2017.

The present invention relates to the technical field of supporting patients in the repeated taking of medications in the context of a therapeutic treatment. The subject matter of the present invention is a method, a system and a computer program product, which monitor the taking of medicines by a patient and inform the patient or a physician or another person if a dose of medication should not be taken, so as to optimize the effectiveness of the treatment or to reduce risks.

There are a large number of people who have to take medication over a prolonged period of time or permanently.

For example, patients with heart disease (e.g. in the case of artificial heart valve replacement, heart malformations, cardiac arrhythmias, cardiac insufficiency) and those with repeated cases of thrombosis and pulmonary embolisms should receive long-term anticoagulant therapy, also known colloquially as "blood thinners".

In particular with such long-term medication usage, adherence is an important factor. Adherence refers to the extent to which a person's behavior with regard to medication taking, diet maintenance and/or lifestyle changes conforms to the agreed recommendations of a medical practitioner.

There are various methods for determining adherence, which are used in clinical trials and in treatment control. They can be divided into direct and indirect methods. Examples of direct methods are: direct observation (of the intake, for example by a physician), the measurement of drug concentrations in bodily fluids and the measurement of marker substances in the blood, urine or exhaled air. Examples of indirect methods are: medication consumption measurement ("pill count"), patient diaries and electronic monitoring.

The patient interview is the most common method of determining adherence. However, patients apparently overestimate their adherence, and the data for longer periods of time quickly become inaccurate. More precise values can be obtained by measuring medication levels in the blood. However, this method is cost-intensive and only allows conclusions about the period in which the ingested substance has not yet been metabolized or excreted.

Devices for electronic monitoring are also grouped under the term MEMS (Medication Event Monitoring System(s)). There are various MEMS available on the market. Examples are the "Helping Hand" from Bang & Olufsen Medicom and the smartphone app by the company AiCure for visual confirmation of a drug dose being taken using the smartphone's built-in camera.

The systems available on the market support a patient in the repeated administration of medication portions appropriate to the particular course of treatment.

Events may occur, however, after which otherwise repeatedly taken medicines should not be taken, in fact their continued administration could even endanger the patient's life. As examples, one could cite surgical or comparable interventions (e.g. biopsies, punctures and the like) in such patients who are being treated with anticoagulants or platelet inhibitors. The risk of an increased tendency to bleeding must be taken into account, not only in relation to the surgical intervention, but also to the choice of the anesthesiological procedure (e.g. procedures close to the spinal cord).

There is thus a need to remind patients not only to take regular medication doses, but also to support them in the case of a scheduled event for which taking a medication dose would hamper effective treatment or represents a risk.

This technical object is achieved by means of the subject matter of the independent claims 1, 10 and 15. Preferred embodiments can be found in the dependent claims and the present description.

A first object of the present invention is thus a method comprising the steps
- automated monitoring of repeated taking of medication by a patient
- registering an event for which taking the medication is contraindicated
- identifying a discontinuation time after which the medication should no longer be taken on the basis of the contraindication
- registering an attempted or actual ingestion of the medication after the discontinuation time
- in the event of attempted ingestion: sending a warning to the patient that the medication should not be taken
- in the event of an actual ingestion: sending a message informing the patient and/or another person related to the event about the actual ingestion.

A further object of the present invention is a system comprising
- means for the automated monitoring of repeated taking of medication by a patient
- means for registering an event for which taking the medication is contraindicated
- means for identifying a discontinuation time after which the medication should no longer be taken on the basis of the contraindication
- means for registering an attempted or actual ingestion of the medication after the discontinuation time
- means for sending a warning to the patient that the medication should not be taken and/or for sending a message informing the patient and/or another person related to the event about the actual ingestion.

Additional objects of the present invention are a computer program product comprising a data carrier and program code which is stored on the data carrier and which causes a computer unit, in the memory of which the program code is loaded, to execute the following steps:
- receiving an event time for an event, for which taking a medication is contraindicated
- identifying a discontinuation time from which the medication should no longer be taken on the basis of the contraindication
- registering an attempt to take or actually taking of a portion of the medication by a patient
- sending a warning to the patient that the portion of medication should not be taken, and/or to another person related to the event about the actual ingestion.

The invention is explained in more detail below, without distinguishing between the invention objects (method, system, computer program product). The following explanations are intended instead to apply to all objects of the invention in an analogous manner, regardless of the context in which they are given (method, system, computer program product).

If in the present description or in the claims steps in a sequence are mentioned, this does not necessarily mean that the invention is limited to the sequence mentioned. Rather, it is conceivable for the steps to be executed in a different order, or also in parallel with each other; unless a step builds on another step, which makes it mandatory that the dependent step is executed afterwards (which will be clear from the specific case). The sequences given thus represent preferred embodiments of the method according to the invention.

The invention is primarily intended for patients who repeatedly take medicines. The term "repeated taking" should be understood to mean that the patient must take a medication as part of a course of treatment or a preventative measure over a period, which typically lasts for several days, weeks, months, or even years. It could be said that repeated taking within the meaning of the present invention exists if the patient has to take more than five, preferably more than ten, particularly preferably more than twenty, doses of a specific medicinal product at different times. The drug doses can be taken regularly or irregularly. They are normally taken on a regular basis, which means at constant time intervals.

A drug or medical product is a substance or mixture of substances that provides a therapeutic effect. The term is synonymous with the term medication.

The term "taking" or "ingestion" should not be construed restrictively, such that it only means an oral administration of a drug. Rather, the term "taking" covers every conceivable form of application, such as aural, buccal, by inhalation, intra-arterial, intra-articular, intragluteal, intradermal, intramuscular, intraocular, intrauterine, intravenous, intravitreal, intranasal, subcutaneous, rectal, sublingual, subcutaneous, topical, transdermal, vaginal and the like. Preferably, the medication is taken by the patient him/herself; i.e., a medical specialist is not required to administer the medication to the patient. The medication is preferably one that the patient takes orally.

Normally, the medication exists in the form of defined portions, of which a patient should take a defined amount (a portion, two portions, a half portion or the like) at defined times or within defined time periods.

The medication can be in solid form (e.g. in the form of tablets) or liquid form (e.g. as a syrup) or in a gaseous or a mixed form (e.g. as a gel capsule or as an aerosol or as an ointment). It may be a pure substance, a solid compound, a solution, a suspension (e.g. an emulsion or an aerosol) or the like.

In a particularly preferred embodiment the medicine is an anticoagulant or platelet function inhibitor.

Examples of anticoagulants are e.g. rivaroxaban, dabigatran, apixaban, edoxaban, coumarines (e.g. marcumar, warfarin), heparins (such as enoxaparin, dalteparin, tinzaparin, fondaparinux, etc.), factor XIa and factor XI inhibitors.

Examples of other platelet function inhibitors are aspirin, clopidogrel, prasugrel and ticagrelor, cangrelor, elinogrel, abciximab, eptifibatide, tirofiban, vorapaxar, atopaxar, tifacogin, NAPc2.

The first step of the method according to the invention is the automatic monitoring of the repeated taking of a medication by a patient. The term "monitoring the taking" means that it is monitored whether the patient has at least made preparations to take a portion of medication, and/or whether he/she actually has taken a portion of the medication.

The monitoring of the ingestion is carried out in order to increase the adherence. "Adherence" here refers to the extent to which the behavior of the patient in relation to the taking of a medicinal product conforms to the recommendations agreed with the treating physician.

The term "automatic monitoring" means that the patient is supported in the repeated administration of a drug by a technical monitoring unit for treatment with medication (in short: MEMS=Medication Event Monitoring System). The monitoring unit is an integral part of the system according to the invention. The monitoring unit is preferably a portable device that a patient can carry with them (e.g. in the trouser pocket or purse).

The term monitoring unit is understood to mean any electronic system that detects an attempt to take and/or the actual taking of a portion of medication by a person.

The term "attempt to take" is understood to mean measures taken by a person to prepare to take a portion of a medicine. A typical example is the removal of a portion of medicine from its packaging, e.g. the removal of a tablet from a blister pack.

It is conceivable that preparatory measures for taking a portion of medicine are not taken by the patients themselves but, for example, by a physician or a carer or by relatives. For the purposes of the present invention, it is irrelevant whether the preparatory action is carried out by the patient himself or herself or by another person; the present invention is intended to capture all of these possibilities. For the sake of a simpler presentation the invention will be described primarily based on the first option (that the patient takes the preparatory measures), without intending to restrict the invention to this option.

In one embodiment of the present invention the monitoring unit registers whether and when the patient has made preparations for removing a portion from a device for storing the medication and/or whether and when the patient has removed a portion of medication. It is conceivable that before he/she can remove a portion of medication from the storage device, the patient must indicate, for example by pressing a button or by presenting a biometric characteristic (for example, the finger to record a fingerprint in the context of a fingerprint recognition) that he/she would like to remove a dose of medication. In such a case the monitoring unit registers the action of the patient, which is designed to result in a removal of a dose of medication. It is also conceivable, however, that the monitoring unit registers the actual removal of a dose of medication. For example, it is conceivable that by squeezing a portion of a medication out of a blister pack an electrically conductive conductor track is interrupted, for example; this interruption can be detected by an electronic circuit, for example (see, e.g., WO9604881A1 or DE19516076A1).

In another embodiment, the monitoring unit is designed in such a way that it registers the actual taking of a portion of medication by the patient. As an example, the above-mentioned system from the company AiCure could be mentioned. In the case of the AiCure system, the actual taking of a portion of medication is tracked by a smartphone app using the smartphone's camera. Image analysis and image recognition algorithms ensure that the portion of medication and the face of the patient are detected. It is also detected that the patient puts the medication dose into their mouth and swallows.

In a preferred embodiment the monitoring unit is designed in such a way that it reminds the patient (or else the nursing staff or another person) that they are due to take a portion of medication; for example acoustically (e.g. by means of a signal tone or a voice message), visually (e.g. by a flashing light or a text message) and/or by tactile means (for example by means of vibration).

In a further step of the method according to the invention, an event is registered. The event is contraindicated for taking the medication. This means that there are reasons which argue against taking the drug at a time when the drug delivers an effect that will persist at the time of the event.

It is conceivable that taking a portion of medication is not "compatible" with the event. The effect of the medication leads to an effect "which does not suit the event" or is "unwanted" in conjunction with the event.

The patient is normally compelled to take a medication repeatedly; as a consequence of the event, however, he/she should refrain from (further) use.

In a preferred embodiment the event is an event scheduled for the future.

Preferably, the event is a medical intervention, particularly preferably a measure that is associated with bleeding or may cause bleeding.

An intervention in the medical field denotes any active form of treatment, if one were to distinguish it from merely waiting. This includes both therapeutic and preventive measures. In the narrower sense, intervention means is an acute, urgent intervention against a disease process.

Examples of interventions which may be associated with bleeding are surgical procedures (operations), punctures, biopsies, tooth extractions, catheter examinations and the like.

For example, it is conceivable that the effect of the medication represents an (increased) risk (e.g. a safety risk) for the event. For example, it is conceivable that the medicinal product has a "blood thinning" effect and the event planned for the future is an invasive measure. Through the "blood thinning" effect of the drug, there is an increased risk of bleeding that could occur during the invasive measure and/or thereafter that might not be able to be stopped, or only with difficulty.

It is also conceivable, however, that a medicinal product must be ceased on a regular basis. One example is that of contraceptives, which are usually taken over a cycle of 21 days; thereafter, they are paused for a period of 7 days. The patient should thus take a dose of medication for 21 days and is preferably also reminded to do so. If she tries to take a further portion of medication on the 22nd day, however, according to the invention this attempt is detected and appropriate measures are taken.

It is also conceivable that the event is the attainment of an effective level in a patient. An "effective level" refers to the concentration of a drug in the body (or certain parts of the body) of a patient, which is necessary in order to achieve the desired therapeutic effect. It is conceivable that an effective level is reached due to repeated taking of a medical product. It is conceivable that the medication can be discontinued or should be discontinued after the effective level is reached, in order to reduce or prevent side effects. Such an approach could be useful, for example, in the case of antibody therapy.

It is conceivable, however, that the event results from the fact that a parameter in the patient's body assumes a defined value, or reaches a value above or below a threshold value. The parameter can be, for example, the concentration of a drug in the body or in a region of the body; for example, it may be the concentration of a drug in the blood or other body fluid. The parameter can also be the concentration of a biomarker or another measurable substance in the body or excretion products of the body. The parameter may or may not be the body temperature, blood pressure or other physiological variables. Preferably, the parameter is measured using a sensor on or in the patient's body or in a product of the human body (blood, saliva, urine, etc.).

In a further step of the method according to the invention, a discontinuation time is registered. The discontinuation time in a preferred embodiment of the present invention is chronologically prior to the event (preferably planned for the future).

As is well known, a drug reveals its effect over a certain period of time. After a medicine is taken the effect of the drug persists for a certain period of time, which is usually patient-specific.

The discontinuation time is defined in such a way that after this time the drug should no longer be taken, in order to avoid an (unwanted) effect of the drug at the time of the event, or to ensure that the effect remains below a tolerance threshold.

It is conceivable to calculate the discontinuation time based on effective periods. For example, average effective periods or safe effective periods can be used.

An effective period usually begins with the taking of the drug. The average effective period ends when, on average, the effect of the medicine can no longer be observed/measured in patients. The safe effective period ends at the time at which it can be assumed with a probability bordering on certainty that the drug is no longer effective. It is also possible to define other effective periods, however; for example, it is conceivable to define as the effective period the period of time by which the concentration of the drug has fallen to a specific amount e.g. of the maximum value (e.g., 1% or 5% or 10% or similar). Hence in the definition of the effective period it is important first of all to define the effect of a medicinal product which on the occurrence of the event (preferably planned for the future) is still tolerable. Then, the amount of time that elapses until the drug has reached the tolerable effect after being taken by the patient is measured.

Effective time periods can be determined, for example, in clinical trials.

Preferably, the discontinuation time is calculated by subtracting the effective time from the time of the event:

discontinuation time=time of the event scheduled in the future−effective period

In such a case, the effect of a medication which would be taken at the discontinuation time would subside within the effective period and would have a still tolerable effect at the time of the event. Any medication that would be taken after the discontinuation time would still have an effect at the event time which is above the tolerance threshold.

Effective periods can be stored in databases. It is conceivable for the system according to the invention to be able to access such a database to determine the effective period for the respective medication. It is conceivable that the system according to the invention has a memory unit, in which the effective period is stored.

In a preferred embodiment the effective period is calculated for each patient on the basis of patient-specific information. The calculation can be carried out at the time when the registration of the event scheduled in the future takes place; but it can also be carried out sooner or later. The calculation can be carried out with the aid of the system according to the invention.

Patient-specific information that can be included in the calculation of the effective period are, for example, gender, age, weight, height, blood values, genetic features and many others.

It is conceivable to use a pharmacokinetic metabolism model for calculating the patient-specific effective period, such as can be created with PKSim©, for example (http://www.systems-biology.com/products/pk-sim.html).

However, it is also conceivable that the discontinuation time coincides with the time of the event. For example, it is conceivable that a parameter in the patient reaches a defined value or assumes a value above or below a threshold value. This can be the triggering event for the (at least temporary) discontinuation of a medication. After this event time (=discontinuation time), the product should therefore no longer be taken.

In one embodiment of the present invention the system according to the invention registers the attempt to take a portion of medication after the discontinuation time. A person (usually the patient, but also a physician or carer or other person) takes an action which usually causes the patient to a take a portion of medication. The person can take a portion of the medication from a container, for example, this removal being registered. It is also conceivable, however, that the person must operate a switch or present a biometric feature to remove a portion of medication from a container. In such a case, a removal attempt is registered as the operation of the switch or the presentation of a biometric feature. The switch can also be a virtual switch on a screen of a computer unit.

In accordance with the invention, in response to the attempt to take the medication a warning is issued to prevent the actual ingestion. The warning is usually issued to the person who has attempted to take the medication. It is also conceivable, however, to issue one or more warnings to another or to one or more other people.

Such a warning can be audible (e.g. by means of a signal tone or a voice message), visual (e.g. by means of a flashing lamp or a text message) and/or tactile (e.g. by means of vibration).

It is also conceivable that an electronic message is sent to a physician or carer (e-mail, SMS or the like), which informs them of the attempt to take.

In one embodiment of the present invention the system according to the invention registers the actual taking of a portion of medication after the discontinuation time. According to the invention a message is sent in response to the completed ingestion. The message can be directed to the patient, a physician and/or the care staff and/or to another person, who has some connection to the event planned for the future. The message may indicate that a portion of medication has been taken by the patient after the discontinuation time. In response to the completed ingestion the event scheduled for the future can be either canceled or postponed. It is also conceivable that a cancellation or postponement is not possible or not wanted. The message can then be used to take (other) measures to prevent or reduce or compensate for the effects caused by the (unwanted) action of the drug at the time of the scheduled future event.

The system according to the invention can be a single piece of equipment (a single device); but it is also conceivable that the functions that the system according to the invention exercises may be distributed over two or more piece of equipment (devices).

In one embodiment a single device is present. In the device according to the invention the various functionalities which are necessary to implement the present invention are combined in a single device. The device has means for holding a plurality of medication portions. The device may comprise, for example, a container, into which a plurality of medication portions can be filled. But it is also conceivable that the device can receive a replaceable container for medication portions (e.g. a blister strip). The device according to the invention can have means for registering an attempt at removal or an actual taking of a portion of medication. Alternatively, the device according to the invention can have means that registers an actual taking of a portion of medication by a patient. The device comprises a computer unit which is configured so that it can register an event, i.e., the date and the time of the event is recorded. It is conceivable, for example, that the device comprises a calendar function, in which a time of an event can be entered. It is also conceivable, however, that the device is communicatively connected to a sensor. It is conceivable that the sensor measures a parameter in or on a patient's body and transmits measurement values to the device according to the invention. As soon as a transmitted measurement has reached a defined value or assumes a value which is above or below a defined threshold, the computer unit registers the corresponding event. Registering an event usually includes recording the time of the event (event time) as well as information about what type of event it is. The computer unit is also configured such that it can determine, and preferably calculate, a discontinuation time on the basis of the event. If a person attempts to take or actually takes the medication, the computer unit determines whether the attempt to take or the actual ingestion takes place before or after the discontinuation time. If the attempted or actual ingestion occurs after the discontinuation time, the computer unit transmits a message to the person who carried out the attempted or actual ingestion. To do so, the device according to the invention has appropriate means, such as a display screen (for a text or picture message), a small light (for an optical warning signal), a loudspeaker (for a voice message or warning tone) and/or a vibration alarm. The computer unit can also be configured such that it sends a message to a different or additional person, such as an e-mail or SMS or the like to a physician and/or carer or the like.

It is also conceivable that different functionalities necessary for implementing the present invention are distributed over a plurality of separate devices. For example, it is conceivable that there is a separate monitoring unit, which can maintain a communicative connection to a separate computer unit. For example, it is conceivable that the monitoring unit is configured such that it can transmit information about an ingestion attempt or actual ingestion to the separate computer unit (e.g. via Bluetooth, ZigBee, a mobile wireless network or the like). The monitoring unit can be configured such that it communicates any attempted or actual taking of medication; but it is also conceivable that it only communicates attempted or actual ingestion events after the discontinuation time. The separate computer unit, which is preferably embodied as a smartphone, smartwatch or tablet computer, is configured such that it can receive information on attempted or actual ingestion from the monitoring unit and can issue one or more messages.

In addition, it is conceivable that the device according to the invention or the monitoring unit has a blocking function, which is activated as soon as an attempt to take medication after the discontinuation time is registered. The blocking feature prevents, for example, removal of a medication portion, for example by blocking access to the container in which medication portions are stored.

The term computer unit, or computer for short, is preferably understood to mean a universally software-controlled machine for information processing. A computer unit has at least one input unit via which data and control commands can be entered (mouse, trackpad, keyboard, scanner, webcam, joystick, microphone, barcode reader, etc.), a processing unit comprising working memory and processor, with which data and commands are processed, and an output unit to send data out of the system (e.g. monitor, printer, speakers, etc.). Modern computers are often classified into desktop computers, portable computers, laptops, notebooks, netbooks and tablet computers and so-called handheld devices (e.g. smartphones, smartwatches).

The invention is explained in more detail below on the basis of drawings and preferred embodiments without intending to reduce the invention to these examples.

Shown are.

Figure 1:
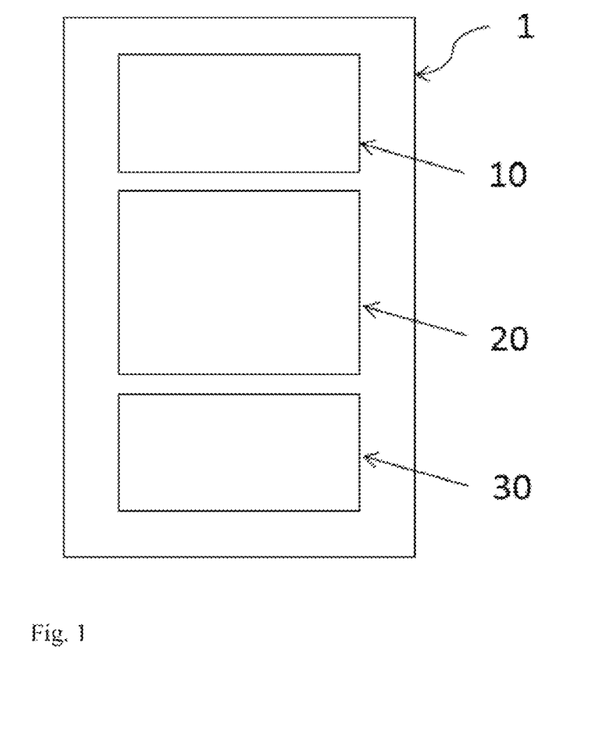
FIG. 1 shows a schematic representation of an embodiment of the system according to the invention.

The system (1) according to the invention comprises a monitoring unit (10), means (20) for recording medication portions, and a computer unit (30).

Figure 2:
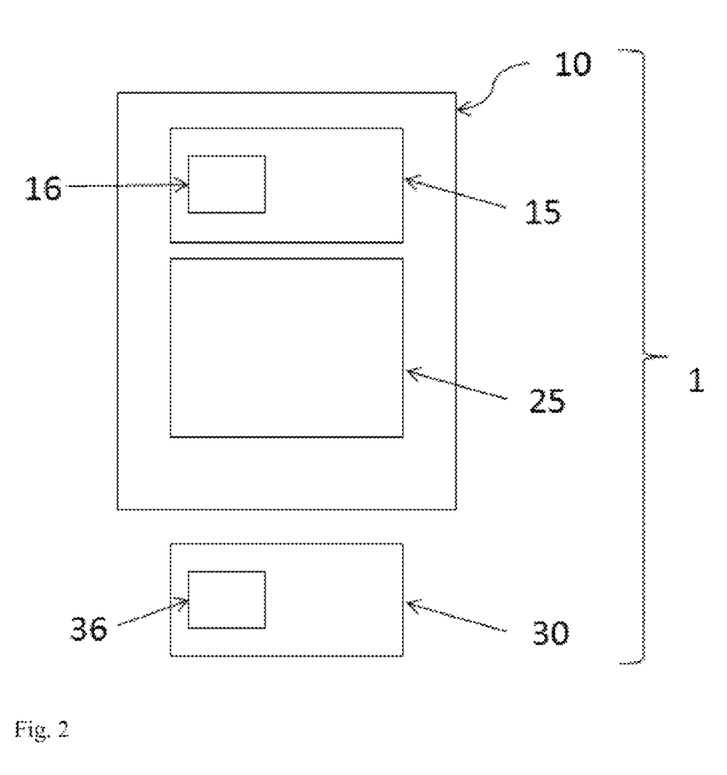
FIG. 2 shows a schematic representation of a further embodiment of the system according to the invention.

The system (1) according to the invention comprises two separate components. One component is a monitoring unit (10), and the other component is a computer unit (30). The monitoring unit (10) has a container (25) for holding portions of medication, and a sensor unit (15). The sensor unit (15) is designed in such a way that it registers a removal and/or an attempted removal of a drug portion from the container (25) and sends a corresponding information item about the removal and/or the removal attempt to the monitoring unit (30) via a transmitter unit (16). The monitoring unit (30) has a receiving unit (36), with which it can receive the information from the transmitter unit (16).

Figure 3:
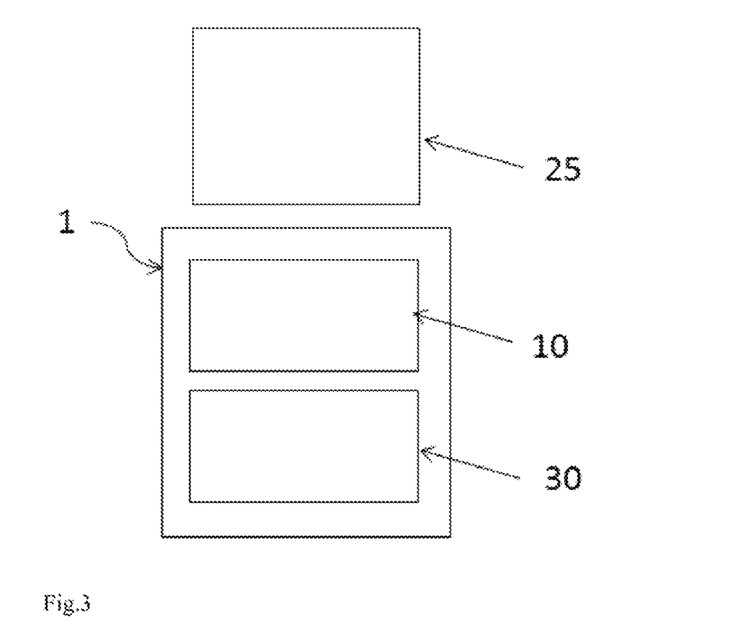
FIG. 3 shows a schematic representation of a further embodiment of the system according to the invention.

A monitoring unit (10) and a computer unit (30) are integrated in a single device (1) (according to the invention). With the monitoring unit (10) a removal and/or an attempted removal of a portion of medication from a separate container (25) can be detected.

Figure 4:
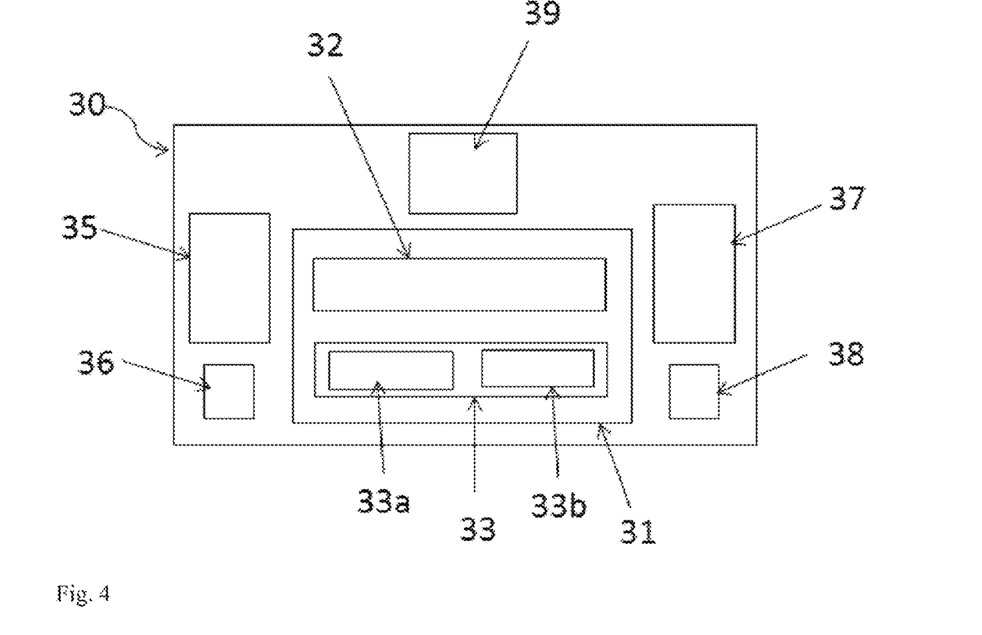
FIG. 4 shows an example schematic structure of a computer unit of the system according to the invention, as is shown in the examples of FIGS. 1, 2 and 3.

The computer unit (30) comprises an input unit (35), with which a user can enter data and control commands. It comprises a processing unit (31) for processing data and control commands. The processing unit (31) has a working memory (32) and a processor (33). The processor (33) comprises a control unit (33*a*) and a calculation unit (33*b*). The computer unit (30) also comprises an output unit (37), with which data can be output. The computer unit (30) also comprises a data memory (39), a receiving unit (36), with which signals and/or data can be received from external devices, and a transmitter unit (39), with which signals and/or data can be sent to external devices.

Figure 5:
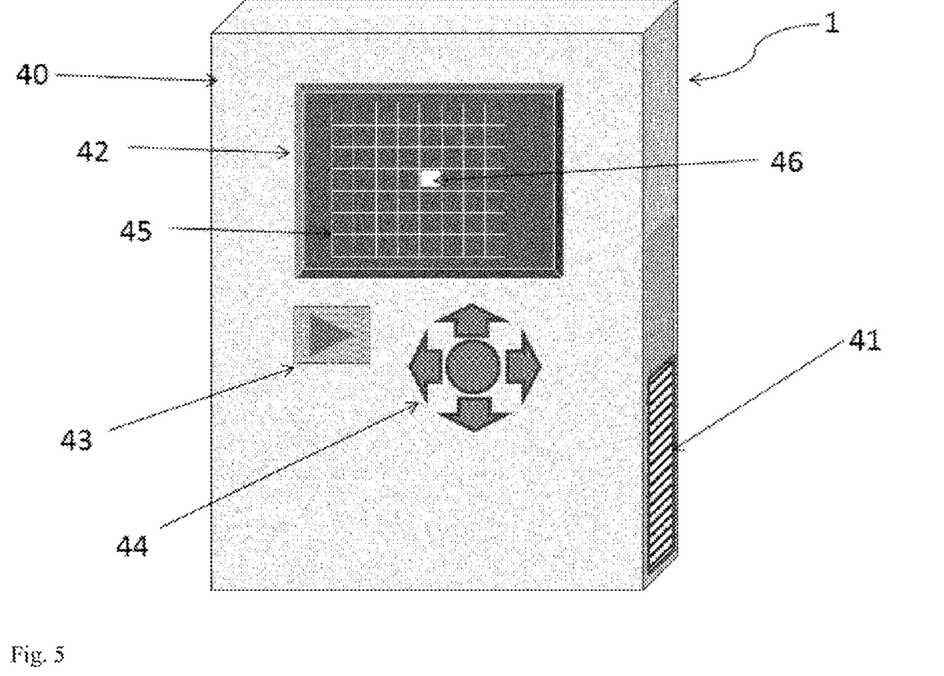

FIG. 5 shows an example of a system (1) according to the invention, in which a computer unit, a monitoring unit and a container for holding medication portions are integrated in a single device. The system (1) according to the invention is designed as a portable handheld device. All components are accommodated in a housing (40). The housing contains an internal space, in which medication portions can be stored (not explicitly identifiable in FIG. 5). The medication portions can be extracted individually through an opening which is closed with a cover (41). The cover (41) is pushed upwards to open the container. The system according to the invention has an output device, embodied as a screen (42). To enter data and control commands, buttons (43, 44) are provided as input units. The screen (42) shows a schematic representation of a calendar (45). The calendar (45) contains an entry for an event (46) for which the use of the medication is contraindicated, but it may also be the case that the event (46) registered in the calendar (45) is the discontinuation time after which the medication should no longer be taken.

The following is possible:

A user uses the system (1) according to the invention for taking the recurrent medication doses.

The user has entered an event (46) in the calendar (45) using the buttons (43, 44), for which taking the medication is contraindicated.

The system according to the invention is configured in such a way that it calculates a discontinuation time from when the user should no longer take a dose of medication due to the upcoming event.

The system according to the invention is configured in such a way that it registers an ingestion attempt.

If the ingestion attempt takes place after the discontinuation time and before the event, a warning message is displayed on the screen (42), that the user should not take a dose of medication due to the upcoming event.

For example, the cover (41) could be locked and the lock could be opened by merely pressing a button, for example the button (43). If the user operates the button (43) to unlock the cover after the discontinuation time and before the event, the warning message could be displayed.

The system could be configured to remind the user about the recurring need to take a portion of medication, as long as the discontinuation time has not yet been reached.

The system according to the invention could be configured so that it sends a message to a physician if the user has taken a portion of medication after the discontinuation time.

Figure 6:
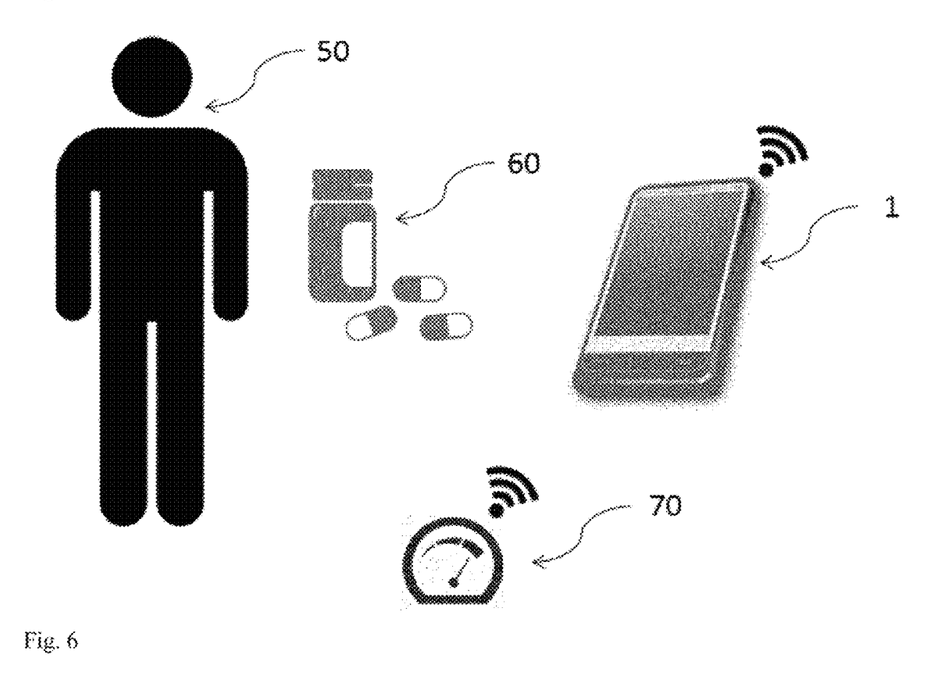

FIG. 6 shows a further embodiment of the present invention. A patient (50) in the context of a course of treatment must repeatedly take a medication (60) in the form of individual portions of the medication (here represented by the three capsules). The system according to the invention is embodied as a smartphone (1), on which the computer program according to the invention is installed. It is conceivable that the smartphone (1) is configured in such a way that it reminds the patient to take a medication portion (or a number of portions) at specific times. The smartphone (1) is further configured in such a way that by means of a sensor (70) it registers the occurrence of an event, for which continuing to take the medication (60) is contraindicated. To this end the sensor (70) has a transmitting unit and the smartphone (1) has a receiver unit (represented by the radio icon). For example, it is conceivable that the sensor measures a parameter in or on the body of the patient (50) or a parameter in a bodily fluid (blood, saliva, urine or the like) of the patient (50). It is conceivable that the sensor (70) transmits values measured at defined times to the smartphone (1) or the smartphone requests measurements from the sensor (70) at defined times. It is also conceivable that the sensor is configured so that it only transmits data to the smartphone (1) on defined upper or lower limits being exceeded or undershot. It is conceivable that the smartphone (1) is configured so that it compares the data received by the sensor (70) with reference data that are stored (saved) in the smartphone (1) in a storage unit, and upon reaching defined states transmits a warning notice to the patient (50) and/or to another person, such as a physician. The warning should then serve to stop the patient (50) from taking another dose of the medication (60).

Figure 7:
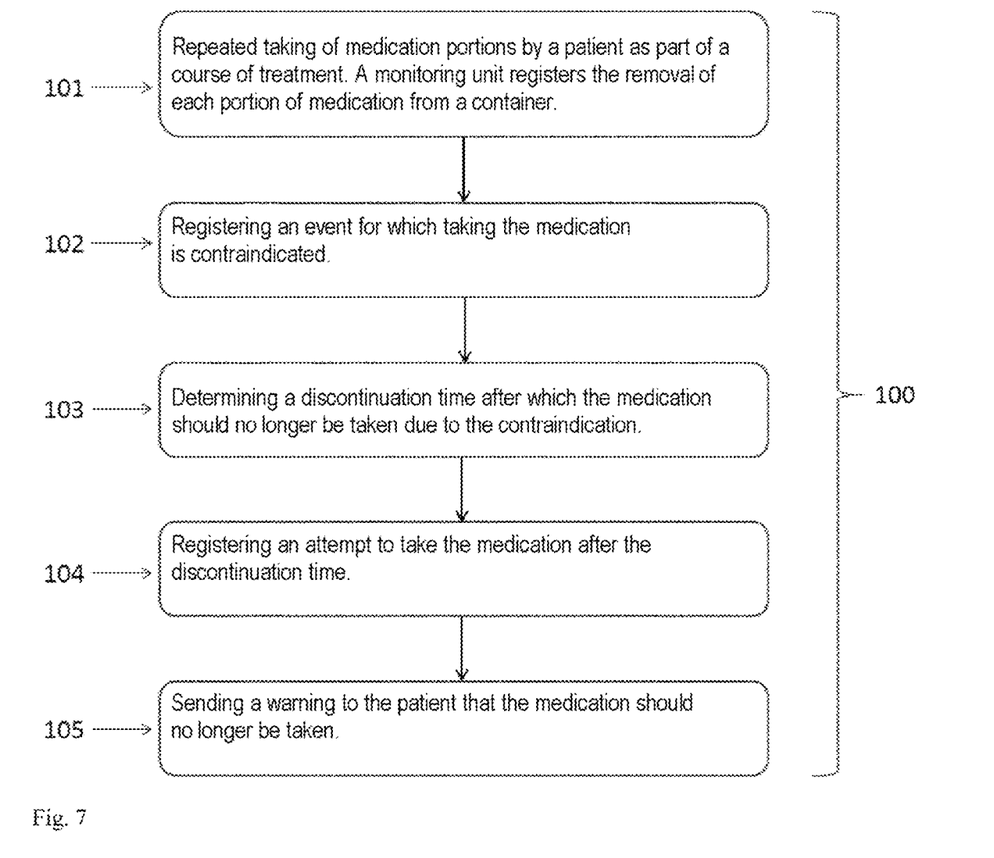

FIG. 7 shows an example of an embodiment of the method (100) according to the invention, comprising the steps (101), (102), (103), (104) and (105). A first step (101) symbolizes the repeated taking of medication portions by a patient in the context of a course of treatment. The patient is supported in this by a monitoring unit; the monitoring unit registers the extractions of the medication portions from their container. In a further step (102) an event is registered for which the further use of the medication is contraindicated. It is conceivable, for example, that the medication is an anticoagulant or platelet function inhibitor, and the patient receives the notification of a pending intervention which may be associated with bleeding. It is conceivable that the patient enters the event in a virtual calendar, which can be an integral part of the monitoring unit or a computer unit. In order to reduce the risk of uncontrollable bleeding, the "blood-thinning agent" should be discontinued in a timely manner before the event (intervention), i.e., no longer taken. In a further step (103) a discontinuation time is determined accordingly, after which the medication is discontinued due to the contraindication, i.e., should no longer be taken. It is conceivable that a physician informs the patient of the discontinuation time. It is also conceivable that the monitoring unit or the computer unit calculates the discontinuation time. It is conceivable that the discontinuation time is entered in a virtual calendar of the monitoring unit or the computer unit. In a further step (104) the monitoring unit registers an ingestion attempt after the discontinuation time. In a further step (105) the monitoring unit or the computer unit sends a warning notice to the patient that the medication should no longer be taken.

Figure 8:
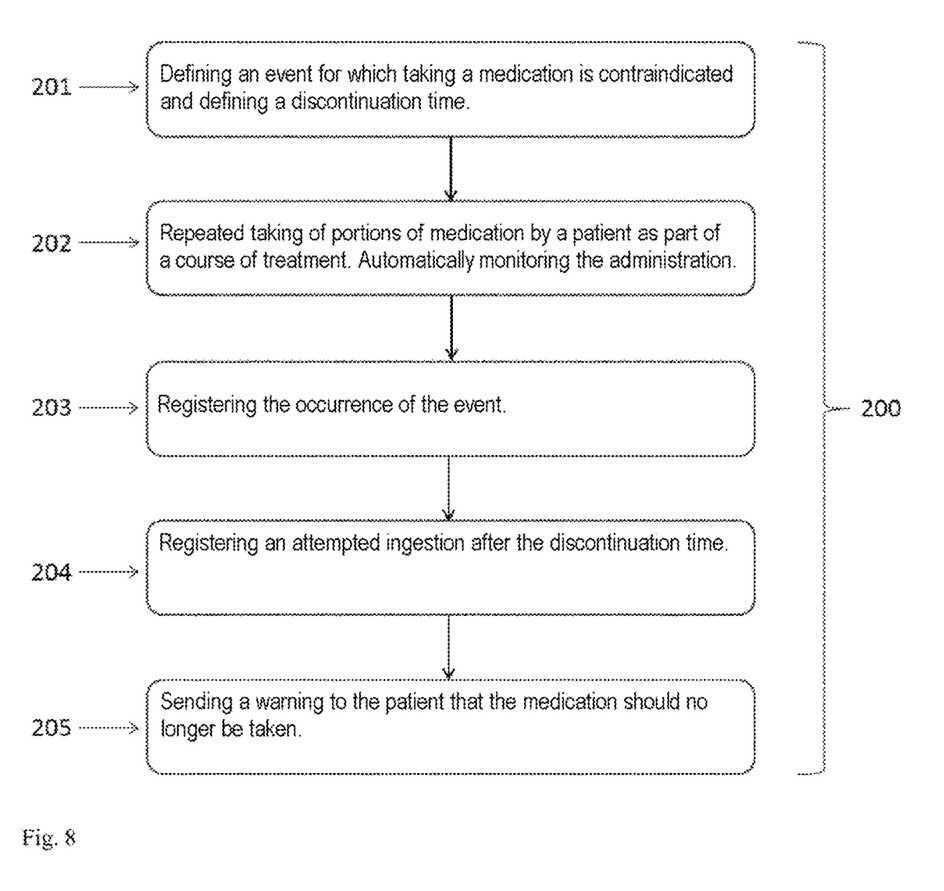

FIG. 8 shows a further embodiment of the method (200) according to the invention, comprising the steps (201), (202), (203), (204) and (205). In a first step (201) an event is defined for which the taking of a medicinal product is contraindicated, and a discontinuation time is defined. In this example it is assumed that the discontinuation time coincides with the timing of the event, i.e. after the occurrence of the event no further medication portions should be taken. Defining the event involves the definition of one or more conditions that must be met in order that the event is deemed to have occurred. It is conceivable, for example, that a parameter has exceeded or fallen below a defined limit value. The parameter could be a physiological parameter of the patient, for example, a concentration of a substance in the patient's body. In a further step (202), the repeated taking of portions of medication by a patient in the context of a course of treatment is automatically monitored by a monitoring unit; i.e. the monitoring unit detects whether the patient has taken a portion of medication or whether the patient has attempted to take the medication. In a further step (203), the occurrence of the event is registered. These are therefore the conditions that have been defined in step (201). By means of the monitoring unit, in a further step (204) an attempt to take a portion of the medication by the patient after the discontinuation time is registered. In a further step (205) the monitoring unit or a computer unit sends a warning to the patient that the medication should no longer be taken.

Figure 9:
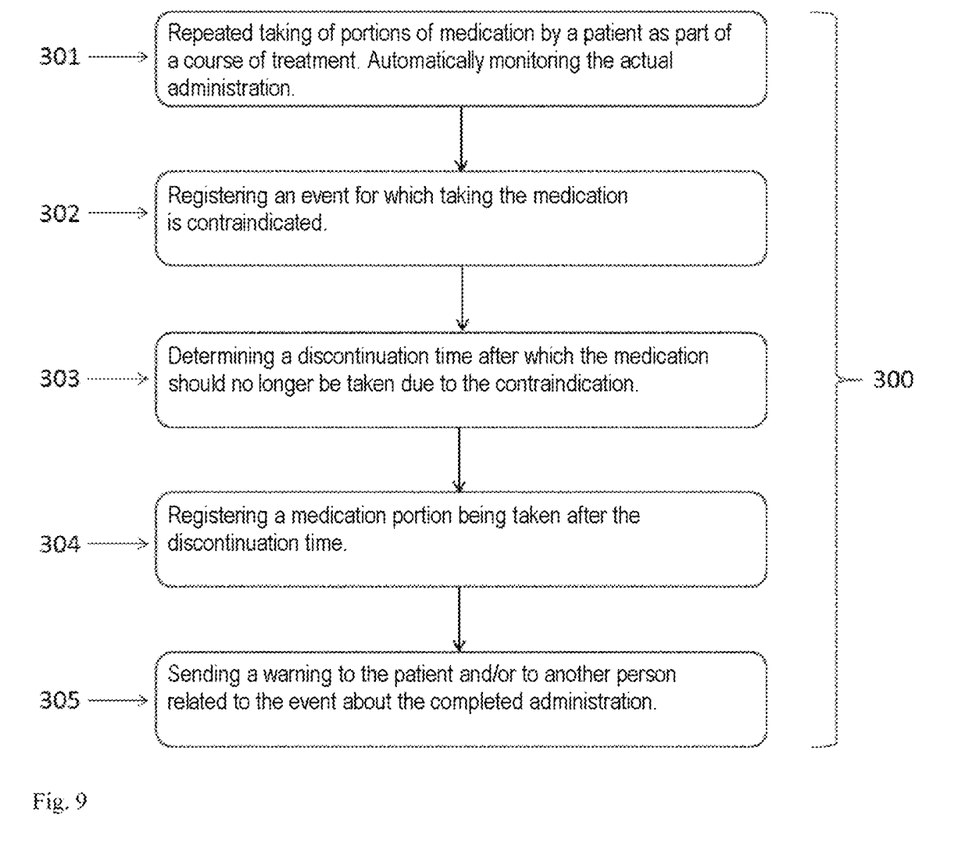

FIG. 9 shows a further exemplary embodiment of the method (300) according to the invention, comprising the steps (301), (302), (303), (304) and (305). A first step (301) symbolizes the repeated taking of medication portions by a patient in the context of a course of treatment. The patient is supported in this by a monitoring unit; the monitoring unit registers the actual taking of the medication portions by the patient. In a further step (302) an event is registered for which the further use of the medication is contraindicated. It is conceivable for the patient to enter the event in a virtual calendar. In a further step (303) a discontinuation time is determined, after which due to the contraindication the medication is discontinued, i.e., should no longer be taken. It is conceivable that the discontinuation time is entered in a virtual calendar. In a further step the monitoring unit (304) registers the actual taking of a medication portion by the patient after the discontinuation time. In a further step (304) the monitoring unit or a computer unit sends a message informing the patient and/or another person connected to the event about the completed ingestion.

Other examples of the present invention are:
1. a method comprising the steps
   automated monitoring of repeated taking of medication by a patient
   registering an event for which taking the medication is contraindicated
   identifying a discontinuation time, from which the medication should no longer be taken on the basis of the contraindication
   registering an attempted or actual taking of the medication after the discontinuation time
   in the event of attempted ingestion: sending a warning to the patient that the medication should not be taken
   in the event of an actual ingestion: sending a message informing the patient and/or another person related to the event about the actual ingestion.
2. the method according to example 1, wherein the event is an event scheduled in the future and the discontinuation time occurs prior to or coincides with the time of the event scheduled in the future.
3. the method according to example 2, the discontinuation time being calculated according to the formula:

$$\text{discontinuation time} = \text{time of the event scheduled in the future} - \text{effective duration}.$$

4. the method according to example 3, wherein the effective period is computed and used to calculate patient-specific information.
5. the method according to any one of examples 1 to 4, wherein the event is a medical intervention on the body of the patient, which is associated with bleeding or the risk of bleeding.
6. the method according to any one of examples 1 to 5, wherein an actual ingestion is registered and the event scheduled for the future is postponed or cancelled as a result of taking the medication, or measures are taken to prevent or reduce or compensate for the effect of the drug existing at the time of the event.
7. the method according to any one of examples 2 to 6, wherein the medication is an anticoagulant or platelet function inhibitor.
8. the method according to example 1, the discontinuation time coinciding with the time of the event or the discontinuation time being after the time of the event.
9. the method according to any one of examples 1 to 8, wherein the event is characterized in that a parameter in the patient's body assumes a defined value, or reaches a value above or below a threshold.
10. a device comprising
    a plurality of portions of a medication
    means for the automated monitoring of repeated taking of medication by a patient
    means for registering an event for which taking the medication is contraindicated
    means for identifying a discontinuation time after which the medication should no longer be taken on the basis of the contraindication
    means for registering an attempted or actual taking of the medication after the discontinuation time
    means for sending a warning to the patient that the medication should not be taken and/or for sending a message informing the patient and/or another person related to the event about the completed ingestion.

11. a device according to example 10, characterized in that the device has a blocking feature that is activated as soon as an ingestion attempt is registered after the discontinuation time, wherein the blocking feature prevents a person from taking a dose of medication.

12. a system comprising a monitoring unit and a computer unit with means for registering an event and for determining a discontinuation time on the basis of the registered event, the monitoring unit being configured so as to detect an attempt to take or an actual medication dosage being taken by a person and transmits information about the attempted or actual taking of medication to the computer unit
the computer unit being configured in such a way that the information about the attempted or actual ingestion is received by the monitoring unit and if the attempted or actual taking of the medication occurs after the discontinuation time, a signal is sent to the user of the computer unit.

13. a system according to example 12, wherein the computer unit is embodied in the form of a smartphone or tablet computer.

14. a system according to one of the examples 12 to 13, further comprising a sensor which measures a parameter in or on the body of a patient and is configured so that it transmits measured values to the monitoring unit or the computer unit.

15. a computer program product comprising a data carrier and program code which is stored on the data carrier and causes a computer unit, in the memory of which the program code is loaded, to execute the following steps:
receiving an event time for an event for which taking a medication is contraindicated
identifying a discontinuation time from which the medication should no longer be taken on the basis of the contraindication
registering an attempt to take or an actual taking of a portion of the medication by a patient
sending a warning to the patient that the portion of medication should not be taken, and/or to another person related to the event about the actual taking of the medication.

The invention claimed is:
1. A method comprising:
automatically monitoring repeated taking of a medication by a patient using an electronic medication monitor configured to detect attempted or actual takings of the medication by the patient;
registering a future event for which taking the medication is contraindicated;
identifying a discontinuation time after which the medication should no longer be taken on the basis of the contraindication, wherein the discontinuation time occurs prior to or coincides with the future event;
detecting, using the electronic medication monitor, an attempted or actual taking of the medication after the discontinuation time;
in the event that an attempt to take the medication is detected after the discontinuation time: sending a warning to the patient using a transmitter, wherein the warning indicates that the medication should not be taken; and
in the event that an actual ingestion of the medication is detected after the discontinuation time: sending a message to one or more external devices using the transmitter, wherein the message informs the patient and/or another person related to the future event about the actual ingestion.

2. The method of claim 1, wherein the electronic medication monitor registers:
when preparatory measures are performed for taking doses of the medication; and/or
when the patient actually takes the medication doses.

3. The method of claim 1, wherein the patient carries the electronic medication monitor on their person together with doses of the medication, as a mobile device or component of a mobile device in order to increase adherence.

4. The method of claim 1, wherein the discontinuation time is calculated according to the formula:

discontinuation time=time of the future event−effective duration of a dosage of the medication.

5. The method of claim 1, wherein the future event is a medical intervention on the body of the patient that is associated with bleeding or the risk of bleeding, and the medication is an anticoagulant or platelet function inhibitor.

6. The method of claim 1, wherein, in the event that an actual ingestion is detected, the future event is postponed or cancelled as a result of the ingestion, or measures are taken to prevent or reduce or compensate for the effect of the drug existing at the time of the event.

7. The method of claim 1, wherein the future event is characterized in that a parameter in the patient's body or a bodily product of the patient assumes a defined value or reaches a value above or below a threshold.

8. A system, comprising
an electronic medication monitor for detecting attempted or actual takings of a medication by a patient, wherein the electronic medication monitor is configured to automatically monitor repeated taking of the medication by the patient;
one or more processors configured to:
register a future event for which taking the medication is contraindicated, and
identify a discontinuation time after which the medication should no longer be taken on the basis of the contraindication, wherein the discontinuation time occurs prior to or coincides with the future event; and
a transmitter configured to:
in the event that an attempt to take the medication is detected by the electronic medication monitor after the discontinuation time, send a warning to the patient indicating that the medication should not be taken and
in the event that actual ingestion of the medication is detected by the electronic medication monitor after the discontinuation time, send a message to one or more external devices informing the patient and/or another person related to the future event about the actual ingestion.

9. The system of claim 8, wherein the electronic medication monitor and one or more processors are components are two separate mobile devices.

10. The system of claim 8, wherein the electronic medication monitor and the one or more processors are components of a single mobile device.

11. The system of claim 8, further comprising a sensor configured to measure a parameter in or on the body of a patient and/or measure a parameter in a bodily product, and to transmit measured values to the electronic medication monitor or the one or more processors.

12. The system of claim 8, comprising a blocking feature that is activated as soon as an ingestion attempt is registered after the discontinuation time, wherein the blocking feature prevents a dose of medication being taken by a person.

13. A non-transitory computer readable storage medium storing instructions that, when executed by one or more processors of an electronic device, cause the device to:
- automatically monitor repeated taking of a medication by a patient using an electronic medication monitor configured to detect attempted or actual takings of the medication by the patient;
- receive an event time for future event for which taking a medication is contraindicated;
- identify a discontinuation time from which the medication should no longer be taken on the basis of the contraindication, wherein the discontinuation time occurs prior to or coincides with the future event;
- detect, using an electronic medication monitor, an attempt to take or an actual ingestion of a portion of the medication by the patient after the discontinuation time;
- in the event that an attempt to take the medication is detected after the discontinuation time, send a warning, using a transmitter, to the patient that the portion of medication should not be taken; and
- in the event that an actual ingestion is detected after the discontinuation time, send a message to another person related to the future event about the actual ingestion.

* * * * *